United States Patent
Bekel et al.

(10) Patent No.: US 10,717,999 B2
(45) Date of Patent: Jul. 21, 2020

(54) **METHOD FOR THE FERMENTATIVE PRODUCTION OF L-LYSINE USING *C. GLUTAMICUM* STRAINS WITH A MUTATED KUP TRANSPORTER**

(71) Applicant: Evonik Operations GmbH, Essen (DE)

(72) Inventors: Thomas Bekel, Halle (DE); Kornelia Voss, Steinhagen (DE); Georg Thierbach, Bielefeld (DE); Frank Schneider, Halle (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/701,634

(22) Filed: Dec. 3, 2019

(65) Prior Publication Data

US 2020/0190546 A1 Jun. 18, 2020

(30) Foreign Application Priority Data

Dec. 18, 2018 (EP) .................................... 18213573

(51) Int. Cl.
*C12P 13/08* (2006.01)
*C07K 14/435* (2006.01)
*C12N 9/12* (2006.01)

(52) U.S. Cl.
CPC ............ *C12P 13/08* (2013.01); *C07K 14/435* (2013.01); *C12N 9/1217* (2013.01); *C12Y 207/02004* (2013.01)

(58) Field of Classification Search
CPC ....................................................... C12P 13/08
See application file for complete search history.

(56) References Cited

U.S. PATENT DOCUMENTS

| 8,697,850 B2 | 4/2014 | Jessberger et al. |
| 9,422,568 B2 | 8/2016 | Jessberger et al. |
| 2009/0311758 A1 | 12/2009 | Jessberger et al. |
| 2014/0127787 A1 | 5/2014 | Jessberger et al. |

FOREIGN PATENT DOCUMENTS

| WO | 2001/00805 | 1/2001 |
| WO | 2009/141330 | 11/2009 |

OTHER PUBLICATIONS

Extended Search Report dated May 4, 2020 in European Application No. 19215284.1, 6 pages.
European Search Report dated Jun. 17, 2019 in European Application 18213573.1.
Follman et al., Journal of Bacteriology, vol. 191, No. 9, Mar. 6, 2009, pp. 2944-2952.

*Primary Examiner* — Tekchand Saidha
(74) *Attorney, Agent, or Firm* — Grüneberg and Myers PLLC

(57) ABSTRACT

A method is useful for the fermentative production of L-lysine using a *C. glutamicum* strain having a mutated Kup transporter.

12 Claims, No Drawings
Specification includes a Sequence Listing.

METHOD FOR THE FERMENTATIVE PRODUCTION OF L-LYSINE USING *C. GLUTAMICUM* STRAINS WITH A MUTATED KUP TRANSPORTER

CROSS-REFERENCE TO RELATED APPLICATION

The present application claims the benefit to the European application EP 18213573.1, to filed on Dec. 18, 2018, which is incorporated by reference in its entirety.

REFERENCE TO A SEQUENCE LISTING

The present application is accompanied by an ASCII text file as a computer readable form containing the sequence listing, titled "Sequence-Listing-as-filed.txt," created on Tuesday, 15 Nov. 19, 2019, 11:22:59 AM, with the file size of 44,000 bytes, which is incorporated by reference in its entirety. Applicants hereby state that the information recorded in computer readable form is identical to the written (on paper or compact disc) sequence listing.

BACKGROUND OF THE INVENTION

Field of the Invention

L-lysine is produced by fermentation of strains of the species *Corynebacterium glutamicum*. Work is continually being done on improving the production methods.

Improvements may relate to the fermentation technology, to the processing of the fermentation broth to a suitable product form or may relate to the intrinsic performance properties of the microorganism itself.

Discussion of the Background

The nucleotide sequences of the chromosomes of various bacteria strains of the species *Corynebacterium glutamicum* are available at publicly accessible databases and may be used for strain development purposes. One such database is the GenBank database of the NCBI (National Center for Biotechnology Information. U.S. National Library of Medicine 8600 Rockville Pike, Bethesda Md., 20894 USA).

During the annotation procedure for a sequenced chromosome of an organism identified structures such as e.g. genes or coding sequences are furnished with a unique identifier called locus_tag by the supplier of the information to the database.

The nucleotide sequence of the *Corynebacterium glutamicum* ATCC13032 chromosome and its analysis were described e.g. by Nakagawa et al. in EP1108790 A2. The information is available at the NCBI under accession number NC_003450. In the chromosome sequence disclosed under accession number NC_003450 locus_tag NCgl0682 identifies a nucleotide sequence annotated as coding for a K+ transporter. The amino acid sequence of the polypeptide is available under the identifier NP_599944.

The nucleotide sequence of the *Corynebacterium glutamicum* ATCC13032 chromosome and its analysis were independently described by Kalinowski et al. (Journal of Biotechnology 104 (1-3), 5-25 (2003)). The information is available at the NCBI under accession number NC_006958. Locus_tag CGTRNA_RS003565 identifies a nucleotide sequence annotated as coding for a potassium transporter Kup. The old_locus_tag designation cg0817 is also used in the art. The amino acid sequence of the polypeptide is available under the identifier WP_011013837. The nucleotide sequences of locus_tag NCgl0682 and CGTRNA_RS03565 are identical. The amino acid sequence of the Kup transporter is shown as SEQ ID NO:2. The corresponding nucleotide sequence of the kup gene is the gene identified by NCgl0682 and shown under SEQ ID NO: 1.

WO 01/00805 also discloses the kup gene of *Corynebacterium glutamicum* according to SEQ ID NO: 2 as well as other genes of *C. glutamicum* encoding proteins involved in membrane synthesis and membrane transport and generally teaches that modifying *C. glutamicum* strains in these genes increases the production of e.g. L-lysine.

Follmann et al. (Journal of Bacteriology 191(9), 2944-2952, 2009) investigated the potassium transport in *Corynebacterium glutamicum*. They provided experimental evidence that the potential potassium channel CglK is the only functional potassium uptake system in *Corynebacterium glutamicum*. Said potassium channel CglK is encoded by a nucleotide sequence identified by the old locus_tag designation cg0887. Follmann et al. further found that cells lacking the kup gene identified by old locus_tag cg0817 showed no difference in growth as compared to the wild type.

SUMMARY OF THE INVENTION

Object of the present invention is to provide new measures for the fermentative production of L-lysine by bacteria of the species *Corynebacterium glutamicum*.

The object underlying the invention is achieved by the subject matter of following various to embodiments.

1. A method for the fermentative production of L-lysine comprising the steps of providing a bacterium of the species *Corynebacterium glutamicum* having the ability to excrete L-lysine and containing in its chromosome a polynucleotide encoding a polypeptide comprising the amino acid sequence of SEQ ID NO:2, wherein the amino acid glycine at position 344 is substituted by valine, cultivating the bacterium in a suitable medium under suitable conditions, and accumulating L-lysine in the medium to form an L-lysine containing fermentation broth.

2. The method of embodiment 1, wherein in the bacterium the polynucleotide encoding said amino acid sequence comprises the nucleotide sequence of positions 40 to 1923 of SEQ ID NO: 1 the nucleobases at positions 1069 to 1071 being gtt, gtc, gta or gtg.

3. The method of embodiment 2, wherein the nucleobases at positions 1069 to 1071 are gtc.

4. The method of embodiment 1, wherein in the bacterium the polynucleotide encoding said amino acid sequence comprises the nucleotide sequence of positions 40 to 1926 of SEQ ID NO: 1 the nucleobases at positions 1069 to 1071 being gtt, gtc, gta or gtg.

5. The method of embodiment 4, wherein the nucleobases at positions 1069 to 1071 are gtc.

6. The method of embodiment 1, wherein in the bacterium the polynucleotide encoding said amino acid sequence comprises the nucleotide sequence of SEQ ID NO: 1 the nucleobases at positions 1069 to 1071 being gtt, gtc, gta or gtg.

7. The method of embodiment 6, wherein the nucleobases at positions 1069 to 1071 are gtc.

8. The method as described in any of embodiments 1 to 9, further comprising the manufacturing of an L-lysine containing product from the fermentation broth.

9. The method as described in any of the preceding embodiments, wherein the manufacturing comprises a purification step.

10. The method of embodiment 9, wherein said purification step is selected from the group consisting of treatment with activated carbon, ionic exchange and crystallization.

11. The method as described in any of the preceding embodiments, wherein the bacterium contains at least one copy of a polynucleotide coding for a feedback resistant aspartate kinase polypeptide variant desensitized to inhibition by mixtures of L-lysine and L-threonine.

12. The method of embodiment 11, wherein the amino acid sequence of said feedback resistant aspartate kinase polypeptide comprises the amino acid sequence of SEQ ID NO:6 containing isoleucine instead of threonine at position 311.

DETAILED DESCRIPTION OF THE INVENTION

It has been found that modifying L-lysine excreting bacteria of the species *Corynebacterium glutamicum* by exchanging the amino acid glycine at position 344 of the encoded amino acid sequence of the polypeptide shown in SEQ ID NO:2 for a different proteinogenic amino acid, i.e. by L-valine, increased their ability to excrete L-lysine in a fermentative process as compared to the unmodified L-lysine producing bacterium.

The present invention makes available a novel method for the fermentative production of L-lysine comprising the steps of providing a bacterium of the species *Corynebacterium glutamicum*, having the ability to excrete L-lysine, containing in its chromosome a polynucleotide encoding a polypeptide comprising the amino acid sequence of SEQ ID NO:2, wherein the amino acid glycine at position 344 is substituted by valine, cultivating the bacterium in a suitable medium under suitable conditions, and accumulating the L-lysine in the medium to form an L-lysine containing fermentation broth. In such fermentative process the L-lysine production is increased compared to a method comprising the cultivation of an L-lysine secreting bacterium of the species to *Corynebacterium glutamicum* without such substitution.

The amino acid sequence of SEQ ID NO:2, wherein the amino acid glycine at position 344 is substituted by valine, is shown in SEQ ID NO:4.

It was found that the modified bacteria provided in the method according to the invention excreted L-lysine, into a suitable medium under suitable fermentation conditions in an increased manner.

The method according to the invention thus contributes to the improvement of technical and economic aspects of the manufacturing of L-lysine or L-lysine containing products.

In a preferred embodiment the bacterium provided in the method according to the invention contains in its chromosome a polynucleotide encoding an amino acid sequence of a polypeptide comprising the nucleotide sequence of positions 40 to 1923 of SEQ ID NO: 1 the nucleobases from position 1069 to 1071 being gtt, gtc, gta or gtg, preferably gtc.

Particularly preferred is the nucleotide sequence of positions 40 to 1923 of SEQ ID NO: 1 the nucleobase at position 1070 being thymine (t).

The nucleotide sequence of positions 40 to 1923 of SEQ ID NO:1 the nucleotides from positions 1069 to 1071 being gtc is identical to the nucleotide sequence of positions 40 to 1923 of SEQ ID NO:3.

In another preferred embodiment the bacterium provided in the method according to the invention contains in its chromosome a polynucleotide encoding an amino acid sequence of a polypeptide comprising the nucleotide sequence of positions 40 to 1926 of SEQ ID NO: 1 the nucleobases from position 1069 to 1071 being gtt, gtc, gta or gtg, preferably gtc.

Particularly preferred is the nucleotide sequence of positions 40 to 1926 of SEQ ID NO: 1 the nucleobase at position 1070 being thymine (t).

The nucleotide sequence of positions 40 to 1926 of SEQ ID NO: 1 the nucleotides from to positions 1069 to 1071 being gtc is identical to the nucleotide sequence of positions 40 to 1926 of SEQ ID NO:3.

In another preferred embodiment the bacterium provided in the method according to the invention contains in its chromosome a polynucleotide encoding an amino acid sequence of a polypeptide comprising the nucleotide sequence of SEQ ID NO: 1 the nucleobases from position 1069 to 1071 being gtt, gtc, gta or gtg, preferably gtc.

Particularly preferred is the nucleotide sequence of SEQ ID NO: 1 the nucleobase at position 1070 being thymine (t).

The nucleotide sequence of SEQ ID NO: 1 the nucleotides from positions 1069 to 1071 being gtc is identical to the nucleotide sequence of SEQ ID NO:3.

The term L-lysine, where mentioned herein, in particular in the context of product formation, also comprises their ionic forms and salts, for example L-lysine mono hydrochloride or L-lysine sulfate.

For practicing the present invention bacteria of the species *Corynebacterium glutamicum* are used. Suitable bacteria for the method of this invention are L-lysine excreting strains of *Corynebacterium glutamicum*, for example L-lysine excreting strains obtained by one or several steps of strain development from strain ATCC13032 and the like and modified as described in this invention.

Strain ATCC13032 (also available as DSM20300) is the taxonomic type strain of the species *Corynebacterium glutamicum*. A taxonomic study of this group of bacteria based on DNA-DNA hybridization was done by Liebl et al. (International Journal of Systematic Bacteriology 41(2), 255-260, 1991). A comparative analysis of various strains of the species *Corynebacterium glutamicum* based on genome sequence analysis was provided by Yang and Yang (BMC Genomics 18(1):940).

A multitude of L-lysine excreting strains of the genus *Corynebacterium*, in particular of the species *Corynebacterium glutamicum* were obtained in the art during the past decades to starting from strains such as ATCC13032, ATCC14067, ATCC13869 and the like. They were obtained as a result of strain development programs using inter alia methods like classical mutagenesis, selection for antimetabolite resistance as well as amplification and promotor modification of genes of the biosynthetic pathway of the L-lysine by genetic engineering methods.

L-lysine excreting strains of the species *Corynebacterium glutamicum* are widely known in the art and can be modified as described in the present invention. For example, U.S. Pat. No. 7,338,790 B2 describes strain DM1797. It is deposited at the DSMZ (Braunschweig, Germany) under accession number DSM16833. DM1797 is an aminoethylcystein resistant mutant of strain ATCC13032 obtained after N'-methyl-N-nitro-nitrosoguanidine mutagenesis. For example, Blombach et al. (Applied and Environmental Microbiology 75(2), 419-427, 2009) describe strain DM1933, which is deposited under accession number DSM25442. Strain DM1933 was obtained from ATCC13032 by several steps of strain development. Furthermore L-lysine excreting *Corynebacterium glutamicum* strain DM2031, deposited at the DSMZ (Braunschweig, Germany) under the accession number DSM32514 may be used. Strain DM2031 is a further developed derivative of DM1933 having enhanced L-lysine excretion ability. Other L-lysine excreting *Corynebacterium glutamicum* strains are e.g. described in WO2008033001 A1 and EP0841395 A1.

L-lysine excreting strains of the species *Corynebacterium glutamicum* typically contain a polynucleotide coding for a feedback resistant aspartate kinase polypeptide variant. A feedback resistant aspartate kinase polypeptide variant means an aspartate kinase which is less sensitive, or desensitized, to inhibition by mixtures of L-lysine and L-threonine, e.g. 10 mM each, or mixtures of the L-lysine analogue S-(2-aminoethyl)-L-cysteine and L-threonine, e.g. 50 mM S-(2-aminoethyl)-L-cysteine and 10 mM L-threonine, when compared to the wild form of the enzyme, which is contained in wild strains like for example ATCC13032. ATCC14067 and ATCC13869. The EC number for aspartate kinase is EC 2.7.2.4. Descriptions of polynucleotides of *Corynebacterium glutamicum* encoding a feedback resistant aspartate kinase polypeptide variant are for example given in U.S. Pat. Nos. 5,688,671, 6,844,176 and 6,893,848. A summarizing list can be found inter alia in WO2009141330 A1. The symbol used in the art for a gene coding for an aspartate kinase polypeptide is lysC. The abbreviation ask is also found. In case the gene codes for a to feedback resistant polypeptide variant the art typically uses symbols like lysC$^{fbr}$ with fbr indicating feedback resistance. The art also uses the term aspartokinase for aspartate kinase.

Accordingly, said L-lysine excreting strains of the species *Corynebacterium glutamicum* modified as described in the present invention preferably contain at least one copy of a polynucleotide coding for a feedback resistant aspartate kinase polypeptide variant desensitized to inhibition by mixtures of L-lysine and L-threonine.

Said polynucleotide encoding said aspartate kinase polypeptide variant can be expressed by its natural promoter, i.e. the promoter contained in strain ATCC13032, or any other suitable promoter known in the art.

SEQ ID NO:5 shows the nucleotide sequence of the coding sequence of the aspartate kinase polypeptide of strain ATCC13032 and SEQ ID NO:6 the amino acid sequence of the encoded polypeptide. It is known in the art (see U.S. Pat. No. 6,893,848) that exchange of the amino acid Thr at position 311 of SEQ ID NO:6 for Ile imparts the enzyme feedback resistance to inhibition by mixtures of L-lysine and L-threonine.

Accordingly, it is preferred that the amino acid sequence of said feedback resistant aspartate kinase polypeptide comprises the amino acid sequence of SEQ ID NO:6 containing isoleucine instead of threonine at position 311.

Said amino exchange can be achieved by exchanging the nucleobase cytosine (c) at position 932 of SEQ ID NO:5 to give thymine (t). The acc codon for threonine is thus altered to the atc codon for isoleucine.

It is further known in the art that exchange of the gtg start codon of the coding sequence for the aspartate kinase polypeptide for atg enhances expression of the polypeptide (see e.g. EP2796555 A2).

Accordingly, it is preferred that the sequence coding for a feedback resistant aspartate kinase polypeptide begins with an atg start codon.

The term DSM denotes the depository Deutsche Sammlung für Mikroorganismen und Zellkulturen (DSMZ) located in Braunschweig, Germany. The term ATCC denotes the depository American Type Culture Collection located in Manassas, Va. US.

*Corynebacterium glutamicum*, in particular strain ATCC13032 and L-lysine excreting strains obtained therefrom during a strain development program, contain in their chromosome a, in particular one, gene encoding a polypeptide comprising the amino acid sequence of SEQ ID NO:2. The coding sequence may contain silent mutations which do not alter the amino acid sequence of the polypeptide. This context is also known as degeneracy of the genetic code in the art.

During the work for the present invention it was found that modifying L-lysine excreting bacteria of the species *Corynebacterium glutamicum* by exchanging the amino acid glycine at position 344 of the encoded amino acid sequence of the polypeptide shown in SEQ ID NO:2 for a different proteinogenic amino acid, i.e. by valine, increased their ability to excrete L-lysine in a fermentative process as compared to the unmodified bacterium.

The skilled artisan is aware of a number of methods of mutagenesis how to achieve said modification in the *Corynebacterium glutamicum*.

A mutant bacterium according to the invention can be obtained by classical in vivo mutagenesis executed with cell populations of strains of *Corynebacterium glutamicum* using mutagenic substances, e.g. N-methyl-N'-nitro-N-nitrosoguanidine, or ultra violet light.

The nucleotide sequence comprising the site of mutagenesis within the gene can be amplified by PCR using primers selected from SEQ ID NO: 1 or SEQ ID NO:3. By sequencing the PCR product the desired mutants are identified. Details concerning this approach can be found inter alia in U.S. Pat. No. 7,754,446. Real-time PCR in combination with FRET hybridization probes may also be used for mutation detection. The term FRET is the abbreviation for fluorescence resonance energy transfer. Cyril D S Mamotte (The Clinical to Biochemist Reviews 27, 63-75 (2006)) reviews the identification of single nucleotide substitutions using this method.

Another common method of mutating genes of *Corynebacterium glutamicum* is the method of gene replacement described by Schwarzer and Pühler (Bio/Technology 9, 84-87 (1991)) and further elaborated by Schafler et al. (Gene 145, 69-73 (1994)).

Peters-Wendisch et al. (Microbiology 144, 915-927 (1998)) used the gene replacement method to inactivate the pyc gene of *Corynebacterium glutamicum* encoding pyruvate carboxylase. In U.S. Pat. No. 7,585,650 the method was applied to the zwf gene to realize an amino acid exchange at position 321 of the amino acid sequence of the Zwf sub-unit of the glucose 6-phosphate dehydrogenase. In U.S. Pat. No. 7,754,446 the method was applied to the rel gene to realize an amino acid exchange at position 38 of the amino acid sequence of the GTP-pyrophosphate kinase polypeptide.

In the gene replacement method, a mutation, for example, a deletion, insertion or substitution of at least one nucleobase, is provided by an isolated polynucleotide comprising the nucleotide sequence of the gene in question or a part thereof containing the mutation.

In the context of the present invention the nucleotide sequence of the gene in question is the gene identified by NCgl0682 also known as kup gene in the art.

In the context of the present invention the mutation is a substitution of at least one nucleobase located in the codon specifying the amino acid glycine at position 344 of the encoded amino acid sequence (see SEQ ID NO: 1 and SEQ ID NO:2) of the polypeptide.

As a consequence of said mutation the codon specifies a proteinogenic amino acid different from glycine, preferably leucine, isoleucine or valine, particularly preferred valine. The codons specifying valine are gtt, gtc, gta and gtg. The codon gtc is preferred.

The codon for the amino acid at position 344 has the position from 1069 to 1071 in SEQ ID NO: 1 or SEQ ID NO:3. The nucleotide sequence from position 1069 to 1071, in particular the nucleotide at position 1070, may also be referred to as site of mutation.

The mutated nucleotide sequence of the gene in question or a part thereof containing the mutation comprises i) a nucleotide sequence at the 5'-end of the site of mutation, which is also referred to as 5'-flanking sequence or upstream sequence in the art, ii) a nucleotide sequence at the 3'-end of the site of mutation, which is also referred to as 3'-flanking sequence or downstream sequence in the art, and iii) the nucleotide sequence of the site of mutation between i) and ii).

Said 5'-flanking sequence and 3'-flanking sequence required for homologous recombination typically have a length of at least 200 bp, at least 400 bp, at least 600 bp or at least 800 bp. The maximum length typically is 1000 bp, 1500 bp or 2000 bp.

An example of a polynucleotide comprising a mutated nucleotide sequence in the context of the present invention is shown in SEQ ID NO:7. The nucleotide sequence of SEQ ID NO:7 from positions 9 to 1724 corresponds to SEQ ID NO:3 from positions 213 to 1928. The polynucleotide shown in SEQ ID NO:7 contains at its 5'- and 3'-end recognition sites for the restriction endonuclease XbaI useful for cloning purposes. SEQ ID NO:7 contains part of the coding sequence of the variant of the NCgl0682 polypeptide described in this invention. The 5'-flanking sequence consists of the nucleotide sequence from positions 9 to 865 of SEQ ID NO:7. The 3'-flanking sequence consists of the nucleotide sequence from positions 867 to 1724 of SEQ ID NO:7. The site of mutation is at position 866 of SEQ ID NO:7.

The mutated nucleotide sequence provided is cloned into a plasmid vector, e.g. pK18mobsacB described by Schafer et al. (Gene 145, 69-73 (1994)), that is not capable of autonomous replication in *Corynebacterium glutamicum*. Said plasmid vector comprising said mutated nucleotide sequence is subsequently transferred into the desired strain of *Corynebacterium glutamicum* by transformation using electroporation or conjugation. After two events of homologous recombination comprising a recombination event within the 5'-flanking sequence provided by the plasmid vector with the homologous sequence of the *Corynebacterium glutamicum* chromosome and a recombination event within the 3'-flanking sequence provided by the plasmid vector with the homologous sequence of the *Corynebacterium glutamicum* chromosome, one effecting integration and one effecting excision of said plasmid vector, the mutation is incorporated in the *Corynebacterium glutamicum* chromosome. Thus the nucleotide sequence of the gene in question contained in the chromosome of said desired strain is replaced by the mutated nucleotide sequence. The presence of the mutation in the desired strain is then confirmed e.g. by analysis of the nucleotide sequence or real-time PCR using FRET as described above.

An event of homologous recombination may also be referred to as crossing over.

It is preferred that the L-lysine excreting *Corynebacterium glutamicum* strains provided for the method of the present invention have the ability to excrete ≥0.25 g/l, preferably ≥0.5 g/l, particularly preferred ≥1.0 g/l, very particularly preferred ≥2.0 g/l of L-lysine in a suitable medium under suitable conditions.

In a fermentative process according to the invention a *Corynebacterium glutamicum* modified in accordance with the present invention and having the ability to excrete L-lysine is cultivated in a suitable medium under suitable conditions. Due to said ability to excrete said L-lysine the concentration of the L-lysine increases and accumulates in the medium during the fermentative process and the L-lysine is thus produced.

A suitable medium used for the production of L-lysine by a fermentative process contains a carbon source, a nitrogen source, a phosphorus source, inorganic ions and other organic compounds as required.

Suitable carbon sources include glucose, fructose, sucrose as well as the corresponding raw materials like starch hydrolysate, molasses or high fructose corn syrup.

As nitrogen source organic nitrogen-containing compounds such as peptones, meat extract, soy bean hydrolysates or urea, or inorganic compounds such as ammonium sulphate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used.

Inorganic ions like potassium, sodium, magnesium, calcium, iron and further trace elements etc. are supplied as salts of sulfuric acid, phosphoric acid or hydrochloric acid.

Other organic compounds mean essential growth factors like vitamins e. g. thiamine or biotin or L-amino acids e.g. L-homoserine.

The media components may be added to the culture in form of a single batch or be fed in during the cultivation in a suitable manner.

During the fermentative process, the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the L-lysine sufficient for being recovered has been formed. The cultivation is then completed. This aim is normally achieved within 10 hours to 160 hours. In continuous processes, longer cultivation times are possible.

Examples of suitable media and culture conditions can be found inter alia in L. Eggeling and M. Bott (Handbook of *Corynebacterium glutamicum*, CRC Press, 2005).

Thus, the fermentative process results in a fermentation broth which contains the desired to L-lysine.

A product containing the L-lysine is then recovered or manufactured in liquid or solid from the fermentation broth.

A "fermentation broth" means a medium in which a *Corynebacterium glutamicum* described in the invention has been cultivated for a certain time and under certain conditions.

When the fermentative process is completed, the resulting fermentation broth accordingly comprises:

a) the biomass (cell mass) of the *Corynebacterium glutamicum* of the invention, said biomass having been produced due to propagation of the cells of said *Corynebacterium glutamicum*,
b) the desired L-lysine accumulated during the fermentative process,
c) the organic by-products accumulated during the fermentative process, and
d) the components of the medium employed which have not been consumed in the fermentative process.

The organic by-products include compounds which may be formed by the *Corynebacterium glutamicum* during the fermentative process according to the present invention in addition to production of the L-lysine.

The fermentation broth is removed from the culture vessel or fermentation tank, collected where appropriate, and used for providing a product containing the L-lysine, in liquid or solid form. The expression "recovering the L-lysine-containing product" is also used for this. In the simplest case, the L-lysine-containing fermentation broth itself, which has been removed from the fermentation tank, constitutes the recovered product.

The fermentation broth can subsequently be subjected to extracting or substantially eliminating water from said fermentation broth. In particular at least 40% (w/w), preferred at least 90% (w/w), more preferred at least 95% (w/w) water are extracted from the to fermentation broth.

Removal of the biomass can be achieved inter alia by centrifugation, filtration or decantation or a combination thereof.

Manufacturing of an L-lysine product may also comprise a purification step. preferably selected from the group consisting ion exchange chromatography, treatment with activated carbon or crystallization.

Thus e. g. a product containing L-lysine×HCl, preferably containing ≥80% L-lysine×HCl, particularly preferred ≥90% L-lysine×HCl or ≥95% L-lysine×HCl can be obtained.

Analysis of L-lysine to determine its concentration at one or more time(s) during the fermentation can take place by separating the L-lysine by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence).

EXPERIMENTAL SECTION

A) Materials and Methods

The molecular biology kits, primers and chemicals used and some details of the methods applied are briefly described herewith.

1. Antibiotics and chemicals a. Kanamycin: Kanamycin solution from *Streptomyces kanamyceticus* from Sigma Aldrich (St. Louis, USA, Cat. no. K0254).

b. Nalidixic acid: Nalidixic acid sodium salt from Sigma Aldrich (St. Louis, USA, Cat. no. N4382).

c. If not stated otherwise, all chemicals were purchased analytically pure from Merck (Darmstadt, Germany), Sigma Aldrich (St. Louis, USA) or Carl-Roth (Karlsruhe, Germany).

2. Cultivation

If not stated otherwise, all cultivation/incubation procedures were performed as follows herewith:

a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 37° C. and 200 rpm.

b. LB agar (MILLER) from Merck (Darmstadt, Germany Cat. no. 110283) was used for cultivation of *E. coli* strains on agar plates. The agar plates were incubated at 37° C. in an INCU-Line® mini incubator from VWR (Radnor, USA).

c. Brain heart infusion broth (BHI) from Merck (Darmstadt, Germany; Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 33° C. and 200 rpm.

d. Brain heart agar (BHI-agar) from Merck (Darmstadt, Germany; Cat. no. 113825) was used for cultivation of *C. glutamicum* strains on agar plates. The agar plates were incubated at 33° C. in an incubator from Heraeus Instruments with Kelvitron® temperature controller (Hanau, Germany).

3. Determining Optical Density a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 660 nm (OD660) with the GENios™ plate reader from Tecan Group AG (Mannedorf, Switzerland).

4. Centrifugation a. Benchtop centrifuge for reaction tubes with a volume up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13.000 rpm).

b. Benchtop centrifuge for tubes with a volume up to 50 ml

Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4.000 rpm.

5. Detection of Mutations Using FRET

The presence of a given mutation, e.g. a nucleobase exchange, was detected by real-time PCR in combination with FRET hybridization probes. The term FRET is the abbreviation for fluorescence resonance energy transfer. As real-time PCR instrument a Lightcycler from Roche Diagnostics® was used (see below).

This method was e. g. used by M. J. Lay and C. T. Wittwer (Clinical Chemistry 42 (12), 2262-2267 (1997)) for the genotyping of factor V Leiden. Cyril DS Mamotte (The Clinical Biochemist Reviews 27, 63-75 (2006) reviews the genotyping of single nucleotide substitutions using this method.

The FRET hybridization donor probe was labelled with the fluorescent dye fluorescein and the acceptor probe with the fluorescent dye LC-Red640. In essence the detection method comprised three steps: colony PCR, probe hybridization and subsequent melting curve analysis. The method is simply referred to as real-time PCR herewith.

a. Primers and Probes

The oligonucleotides used were synthesized by eurofins genomics GmbH (Ebersberg, Germany).

b. Template

As PCR template the total DNA contained in a colony was used. It was prepared by taking cell material with a toothpick from a colony on an agar plate and placing the cell material to directly into the PCR reaction tube. The cell material was heated for 10 sec. with 800 W in a microwave oven type Mikrowave & Grill from SEVERIN Elektrogerate GmbH (Sundem, Germany) and then the PCR reagents were added to the template in the PCR reaction tube.

b. Reaction Mix

The Type-it® Fast SNP probe PCR Kit (Type-it Kit) from Qiagen (Hilden, Germany, Cat.No. 206045) was used for real-time detection of the mutations. Therefore 2.5 µl of the Qiagen Fast SNP Puffer (2×) was mixed with 0.5 µl of each of the LC-PCR-Primers [10 µM] and 0.5 µl of each of the 1:500 diluted acceptor and donor probe [100 pmol/µl] to get the mastermix for the real-time PCR.

TABLE 1

Thermocycling conditions for PCR with the LightCycler® (step 1-3) and melting curve analysis (step 4-6).
PCR-program

| Step | Time [sec.] | T [° C.] | Description |
|---|---|---|---|
| 1 | 15 | 95 | Denaturation step (and Activation of HotStarTaq ™ DNA polymerase) |
| 2 | 05 | 55 | Annealing step |
| 3 | 30 |  | Elongation step Repeat step 1 to 3: 50× |
| 4 | 10 | 95 | Denaturation step |
| 5 | 30 | 40 | Probe hybridisation |
| 6 |  | 40-80 | Melting curve analysis |
| 7 |  | 80-40 | Cooling | c. PCR Cycler

The reactions were carried out in a LightCycler) 2.0 Instrument and analysed with LightCycler® Software 4.1 of Roche Diagnostics (Rotkreuz, Switzerland).

6. Chemical Transformation of *E. coli*

*E. coli* K-12 strain S17-1 was used as donor for conjugational transfer of plasmids based on pK18mobsacB from *E. coli* to *C. glutamicum*. Strain S17-1 is described by Simon. R. et al. (Bio/Technology 1, 784-794, 1983). It is available from the American Type Culture Collection under the access number ATCC47055.

Chemically competent *E. coli* S 17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant were discarded. The cell pellet was resuspended in 20 ml sterile, ice-cold 50 mM $CaCl_2$ solution and incubated on ice for 30 min. After another centrifugation step, the pellet was resuspended in 5 ml ice-cold 50 mM $CaCl_2$ solution and the suspension incubated on ice for 30 min. The cell suspension was then adjusted to a final concentration of 20% glycerol (v/v) with 85% (v/v) sterile ice-cold glycerol. The suspension was divided into 50 µl aliquots and stored at −80° C. To transform S17-1 cells, the protocol according to Tang et al. (Nucleic Acids Res. 22(14), 2857-2858, 1994) with a heat shock of 45 sec. was used.

7. Conjugation of *C. glutamicum*

The pK18mobsacB plasmid system described by Schafer et al. (Gene 145, 69-73, 1994) was used to integrate desired DNA fragments into the chromosome of *C. glutamicum*. A modified conjugation method of Schafer et al. (Journal of Bacteriology 172, 1663-1666, 1990) was used to transfer the respective plasmid into the desired *C. glutamicum* recipient strain.

Liquid cultures of the *C. glutamicum* strains were carried out in BHI medium at 33° C. The heat shock was carried out at 48.5° C. for 9 min. Transconjugants were selected by plating the conjugation batch on EM8 agar (Table 2), which was supplemented with 25 mg/l kanamycin and 50 mg/l nalidixic acid. The EM8 agar plates were incubated for 72 h at 33° C.

TABLE 2

Composition of the EM8 agar

| Components | Concentration (g/l) |
|---|---|
| Glucose (sterile-filtered) | 23 |
| CSL (corn steep liquor; Roquette; solid content 48 ± 2% w/w) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7H_2O$ | 0.5 |
| $FeSO_4 \cdot 7H_2O$ | 0.01 |
| $CuSO_4 \cdot 5H_2O$ | 0.001 |
| $ZnSO_4 \cdot 7H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. An aliquot was taken from the liquid culture suitably diluted and plated (typically 100 to 200 µl) on BHI agar which was supplemented with 10% sucrose. The agar plates were incubated for 48 h at 33° C. The colonies growing on the sucrose containing agar plates were then examined for the phenotype kanamycin sensitivity. To do so a toothpick was used to remove cell material from the colony and to transfer it onto BHI agar containing 25 mg/l kanamycin and onto BHI agar containing 10% sucrose. The agar plates were incubated for 60 h at 33° C. Clones that proved to be sensitive to kanamycin and resistant to sucrose were examined for integration of the desired DNA fragment by means of real-time PCR.

8. Glycerol Stocks of E. coli and C. glutamicum Strains

For long time storage of E. coli- and C. glutamicum strains glycerol stocks were prepared. Selected E. coli clones were cultivated in 10 ml LB medium supplemented with 2 g/l glucose. Selected C. glutamicum clones were cultivated in twofold concentrated BHI medium supplemented with 2 g/l glucose. Cultures of plasmid containing E. coli strains were supplemented with 50 mg/l kanamycin. Cultures of plasmid containing C. glutamicum strains were supplemented with 25 mg/l kanamycin. The medium was contained in 100 ml Erlenmeyer flasks with 3 baffles. It was inoculated with a loop of cells taken from a colony and the culture incubated for about 18 h at 37° C. and 200 rpm in the case of E. coli and 33° C. and 200 rpm in the case of C. glutamicum. After said incubation period 1.2 ml 85% (v/v) sterile glycerol were added to the culture. The obtained glycerol containing cell suspension was then aliquoted in 2 ml portions and stored at −80° C.

9. Cultivation System According to Wouter Duetz (WDS)

The millilitre-scale cultivation system according to Duetz (Trends Microbiol. 2007; 15(10):469-75) was used to investigate the performance of the C. glutamicum strains constructed. For this purpose, 24-deepwell microplates (24 well WDS plates) from EnzyScreen BV (Heemstede, Netherlands; Cat. no. CR1424), filled with 2.5 mL medium were used.

Precultures of the strains were done in 10 ml twofold concentrated BHI medium. The medium was contained in a 100 ml Erlenmeyer flask with 3 baffles. It was inoculated with 100 µl of a glycerol stock culture and the culture incubated for 24 h at 33° C. and 200 rpm.

After said incubation period the optical densities OD600 of the precultures were determined.

The main cultures were done by inoculating the 2.5 ml medium containing wells of the 24 Well WDS-Plate with an aliquot of the preculture to give an optical density OD600 of 0.1.

As medium for the main culture CGXII medium was used. The composition of the CGXII medium is shown in table 3.

TABLE 3

Composition of CGXII medium.

| Components | Concentration (g/l) |
|---|---|
| MOPS (3-(N-Morpholino)propanesulfonic acid) | 42 |
| (NH$_4$)$_2$SO$_4$ | 20 |
| Urea | 5 |
| KH$_2$PO$_4$ | 1 |
| K$_2$HPO$_4$ | 1 |
| MgSO$_4$•7H$_2$O | 0.25 |
| CaCl$_2$ | 0.01 |
| FeSO$_4$•7H$_2$O | 0.01 |
| MnSO$_4$ H$_2$O | 0.01 |
| ZnSO$_4$•7H$_2$O | 0.001 |
| CuSO$_4$•5H$_2$O | 0.0002 |

TABLE 3-continued

Composition of CGXII medium.

| Components | Concentration (g/l) |
|---|---|
| NiCl$_2$•6H$_2$O | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analysed with the blood glucose-meter to OneTouch Vita® from LifeScan (Johnson & Johnson Medical GmbH, Neuss, Germany). After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analysed in the supernatant.

10. Amino Acid Analyser

The concentration of L-lysine and other L-amino acids, e.g. L-valine, in the culture supernatants was determined by ion exchange chromatography using a SYKAM S433 amino acid analyser from SYKAM Vertriebs GmbH (Firstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 l 263 g trisodium citrate, 120 g citric acid, 1100 ml methanol, 100 ml 37% HCl and 2 ml octanoic acid (final pH 3.5) was used. As buffer B an aqueous solution containing in 20 l 392 g trisodium citrate, 100 g boric acid and 2 ml octanoic acid (final pH 10.2) was used. The free amino acids were coloured with ninhydrin through post-column derivatization and detected photometrically at 570 nm.

11. Glucose Determination with Continuous Flow System (CFS)

A SANplus multi-channel continuous flow analyser from SKALAR analytic GmbH (Erkelenz, Germany) was used to determine the concentration of glucose in the supernatant. Glucose was detected with a coupled-enzyme assay (Hexokinase/Glucose-6-Phosphate-Dehydrogenase) via NADH formation.

B) Experimental Results

Example 1

Sequence of the Kup Gene of C. glutamicum Strain DM1933

Strain DM1933 is an L-lysine producer described by Blombach et al. (Applied and Environmental Microbiology 75(2), 419-427, 2009). It can be obtained at the DSMZ under accession number DSM25442.

The nucleotide sequence of the chromosome of strain DM1933 was determined by Illumina whole-genome sequencing technology (Illumina Inc., San Diego, Calif., US). See e.g. Benjak et al. (2015) Whole-Genome Sequencing for Comparative Genomics and De Novo Genome Assembly. In: Parish T., Roberts D. (eds) Mycobacteria Protocols. Methods in Molecular Biology, Vol 1285. Humana Press, NY, US) and Bennet, S. (Pharmacogenomics 5(4), 433-438, 2004).

It was found that the nucleotide sequence of the kup coding sequence (locus_tag NCgl0682) of strain DM1933 including the nucleotide sequence upstream and downstream thereof is identical to that of ATCC13032 shown in SEQ ID NO: 1.

DM1933 contains in its chromosome a variant of the aspartokinase gene encoding a feedback resistant aspartokinase polypeptide. Said feedback resistant aspartokinase polypeptide has the amino acid sequence of SEQ ID NO:6 of the sequence listing, wherein the amino acid threonine (Thr) at position 311 of the amino acid sequence is replaced by isoleucine (Ile). In U.S. Pat. No. 7,338,790 the abbreviation "lysC T311I" is used to indicate said exchange. Blombach et al. use the abbreviation "lysC(T311I)".

Example 2

Construction of Plasmid pK18mobsacB_Kup_G344V

Plasmid pK18mobsacB_kup_G344V was constructed to enable incorporation of the mutation causing the amino acid exchange G344V into the nucleotide sequence of the kup coding sequence of strain DM1933. The plasmid is based on the mobilizable vector pK18mobsacB described by Schafer et al. (Gene 145, 69-73, 1994). For the construction of pK18mobsacB_kup_G344V the kup_G344V polynucleotide according to SEQ ID NO:7 was synthesized and subcloned into pK18mobsacB by GeneArt (ThermoFisher Scientific (Waltham, USA)).

To assemble the plasmid pK18mobsacB_kup_G344V the following steps were done by GeneArt: The two polynucleotides i.e. the vector pK18mobsacB and the polynucleotide kup_G344V were both treated with XbaI, ligated and the ligation mixture used to transform E. coli.

DNA of plasmid pK18mobsacB_kup_G344V was isolated from a transformant.

Example 3

Construction of Strain DM1933_kup_G344V

The plasmid pK18mobsacB_kup_G344V obtained in example 2 was used to incorporate the mutation (see nucleotide position 1070 of SEQ ID NO: I and SEQ ID NO:3 and nucleotide position 866 of SEQ ID NO:7) leading to the amino acid exchange G344V (see nucleotide positions 1069-1071 of SEQ ID NO:1 and SEQ ID NO:3, amino acid position 344 of SEQ ID NO:2 and SEQ ID NO:4 and nucleotide positions 865-867 of SEQ ID NO:7) into the chromosome of the L-lysine producer DM1933.

Chemically competent cells of E. coli strain S17-1 were transformed with plasmid DNA of pK18mobsacB_kup_G344V. The modified conjugation method of Schafer et al. (Journal of Bacteriology 172, 1663-1666, 1990) as described in materials and methods was used for conjugal transfer into the strain DM1933 and for selection of transconjugant clones by virtue of their sucrose resistance and kanamycin sensitivity phenotype.

Transconjugant clones were analyzed by real-time PCR using the Type-it Kit and the primers LC-Ncgl0682_1 and LC-Ncgl0682_2 for PCR amplification and NCgl0682_344_C as acceptor probe and NCgl0682_G344V_A as donor probe for melting curve analysis (table 4).

TABLE 4

List of primers and probes used for real-time PCR.

| name | sequence |
|---|---|
| LC-NCgl0682_1 | ATCAGATACAGGACGCTGAC |
| LC-NCgl0682_2 | AGGTCTGCGGATTCCGTTGG |
| NCgl0682_344_C[1] | TAGATCTGGACTTCCTCTTT |
| NCgl0682_344_A[2] | CACGGATACAAACAGCAATCCATTAACCAGTGGCA |

[1]acceptor probe labelled with LC-Red640 at the 5'-end and phosphorylated at the 3'-end
[2]donor probe labelled with fluorescein at the 3'-end One of the transconjugant clones thus characterized was called DM1933_kup_G344V. A glycerol stock culture of the transconjugant clone was prepared and used as starting material for further investigations.

Thus the kup gene of strain DM1933 was mutated with the effect that the amino acid glycine at position 344 of the amino acid sequence of the encoded Kup polypeptide was replaced by valine.

Example 4

L-Lysine Production by Strain DM1933_Kup_G344V

Strains DM1933 (reference) and DM1933_kup_G344V obtained in example 3 were analyzed for their ability to produce L-lysine from glucose by batch cultivation using the cultivation system according to Wouter Duetz.

As medium CGXII containing 20 g/l glucose as carbon source was used. The cultures were incubated for 45 h until complete consumption of glucose as confirmed by glucose analysis using blood glucose-meter and the concentrations of L-lysine and the optical density OD660 were determined. The result of the experiment is presented in table 5.

TABLE 5

L-lysine production by strain DM1933_kup_G344V.

| strain | L-lysine[1] (g/l) | OD660 |
|---|---|---|
| DM1933 | 3.7 | 9.5 |
| DM1933_kup_G344V | 4.0 | 9.2 |

[1]as L-lysine x HCl

The experiment shows that L-lysine production was increased in strain DM1933_kup_G344V as compared to the parent strain DM1933.

The invention claimed is:

1. A method for fermentative production of L-lysine, comprising:
cultivating a bacterium of the species *Corynebacterium glutamicum* having an ability to excrete L-lysine and containing in the bacterium's chromosome a polynucleotide encoding a polypeptide, comprising the amino acid sequence of SEQ ID NO:2, wherein the amino acid glycine at position 344 is substituted by valine, wherein the cultivating of the bacterium proceeds in a suitable medium under suitable conditions, and
accumulating L-lysine in the medium to form a L-lysine containing fermentation broth.

2. The method of claim 1, wherein, in the bacterium, the polynucleotide encoding said amino acid sequence comprises a nucleotide sequence of positions 40 to 1923 of SEQ ID NO: 1, wherein nucleobases at positions 1069 to 1071 are gtt, gtc, gta or gtg.

3. The method of claim 2, wherein the nucleobases at positions 1069 to 1071 are gtc.

4. The method of claim 1, wherein, in the bacterium, the polynucleotide encoding said amino acid sequence comprises a nucleotide sequence of positions 40 to 1926 of SEQ ID NO:1, wherein nucleobases at positions 1069 to 1071 are gtt, gtc, gta or gtg.

5. The method of claim 4, wherein the nucleobases at positions 1069 to 1071 are gtc.

6. The method of claim 1, wherein, in the bacterium, the polynucleotide encoding said amino acid sequence comprises a nucleotide sequence of SEQ ID NO: 1, wherein nucleobases at positions 1069 to 1071 are gtt, gtc, gta or gtg.

7. The method of claim 6, wherein the nucleobases at positions 1069 to 1071 are gtc.

8. The method as claimed in claim 1, further comprising manufacturing of a L-lysine containing product from the L-lysine containing fermentation broth.

9. The method as claimed in claim 8, wherein the manufacturing comprises a purification step.

10. The method of claim 9, wherein said purification step is at least one selected from the group consisting of treatment with activated carbon, ionic exchange, and crystallization.

11. The method as claimed in claim 1, wherein the bacterium contains at least one copy of a polynucleotide, coding for a feedback resistant aspartate kinase polypeptide variant, desensitized to inhibition by mixtures of L-lysine and L-threonine.

12. The method of claim 11, wherein an amino acid sequence of said feedback resistant aspartate kinase polypeptide comprises the amino acid sequence of SEQ ID NO:6, containing isoleucine instead of threonine at position 311.

* * * * *

SEQUENCE LISTING

<160> NUMBER OF SEQ ID NOS: 11

<210> SEQ ID NO 1
<211> LENGTH: 1963
<212> TYPE: DNA
<213> ORGANISM: Corynebacterium glutamicum ATCC13032

-continued

```
<220> FEATURE:
<221> NAME/KEY: misc_feature
<222> LOCATION: (34)..(37)
<223> OTHER INFORMATION: putative ribosome binding site
<220> FEATURE:
<221> NAME/KEY: CDS
<222> LOCATION: (40)..(1923)
<223> OTHER INFORMATION: coding sequence of NCgl0682
<220> FEATURE:
<221> NAME/KEY: misc_feature
<222> LOCATION: (1070)..(1070)
<223> OTHER INFORMATION: nucleobase guanine
<220> FEATURE:
<221> NAME/KEY: misc_feature
<222> LOCATION: (1924)..(1926)
<223> OTHER INFORMATION: taa stop codon

<400> SEQUENCE: 1
gtcttttctg agcgctagca tttctccact caaaggagc atg ctt aac cgc atg        54
                                           Met Leu Asn Arg Met
                                             1               5 aaa agt gcg cgg cca aaa tca gtc gct cca aaa tcc gga caa gct tta      102
Lys Ser Ala Arg Pro Lys Ser Val Ala Pro Lys Ser Gly Gln Ala Leu
             10                  15                  20 ctc act ctc ggt gcc cta ggt gtt gtg ttc ggc gac atc ggc acc agc      150
Leu Thr Leu Gly Ala Leu Gly Val Val Phe Gly Asp Ile Gly Thr Ser
         25                  30                  35 ccc ctg tac tca ctt cac act gca ttc agc atg cag cac aac aaa gtc      198
Pro Leu Tyr Ser Leu His Thr Ala Phe Ser Met Gln His Asn Lys Val
     40                  45                  50 gaa gtc act cag gaa aat gtg tac ggc atc atc tcc atg gtg ttg tgg      246
Glu Val Thr Gln Glu Asn Val Tyr Gly Ile Ile Ser Met Val Leu Trp
 55                  60                  65 acc atc act ttg atc gtc acc gtc aaa tac gtc atg ctg gtc acc cga      294
Thr Ile Thr Leu Ile Val Thr Val Lys Tyr Val Met Leu Val Thr Arg
 70                  75                  80                  85 gct gac aac caa gga caa ggt ggc atc ctg gcg ctc gtt gct ttg ctg      342
Ala Asp Asn Gln Gly Gln Gly Gly Ile Leu Ala Leu Val Ala Leu Leu
                 90                  95                 100 aaa aac cgt ggg cac tgg gga aaa ttc gtg gca gta gcc ggc atg ttg      390
Lys Asn Arg Gly His Trp Gly Lys Phe Val Ala Val Ala Gly Met Leu
             105                 110                 115 ggc gcc gca ttg ttt tat ggc gat gtg gtg atc acc ccg gcg atc tct      438
Gly Ala Ala Leu Phe Tyr Gly Asp Val Val Ile Thr Pro Ala Ile Ser
         120                 125                 130 gtt ctc agc gca aca gaa ggc ttg acg gtt atc tcc cca agc ttt gag      486
Val Leu Ser Ala Thr Glu Gly Leu Thr Val Ile Ser Pro Ser Phe Glu
     135                 140                 145 cgc ttc att ctg ccc gta tct ctc gca gtt ctg atc gct att ttt gca      534
Arg Phe Ile Leu Pro Val Ser Leu Ala Val Leu Ile Ala Ile Phe Ala
150                 155                 160                 165 atc caa ccg ctc ggt aca gaa aaa gtc ggc aaa gcc ttc ggc ccc atc      582
Ile Gln Pro Leu Gly Thr Glu Lys Val Gly Lys Ala Phe Gly Pro Ile
                 170                 175                 180 atg ttg ctg tgg ttt gtc acc ctt gca gga tgg gga att ccg caa atc      630
Met Leu Leu Trp Phe Val Thr Leu Ala Gly Trp Gly Ile Pro Gln Ile
             185                 190                 195 atc ggg cac cca gaa atc ttg cag agc ttg tct cca cat tgg gcc ctg      678
Ile Gly His Pro Glu Ile Leu Gln Ser Leu Ser Pro His Trp Ala Leu
         200                 205                 210 cgc ttg att gtg gct gag cct ttc caa gca ttt gtg ctg ctt ggt gcc      726
Arg Leu Ile Val Ala Glu Pro Phe Gln Ala Phe Val Leu Leu Gly Ala
     215                 220                 225
```

```
gtt gtc ctg aca gta acg ggt gcg gaa gcg ctc tac gct gat atg ggc      774
Val Val Leu Thr Val Thr Gly Ala Glu Ala Leu Tyr Ala Asp Met Gly
230             235                 240                 245 cat ttt ggg gcg agg cca atc aga gtg gcg tgg ttt tgc gtc gtc atg      822
His Phe Gly Ala Arg Pro Ile Arg Val Ala Trp Phe Cys Val Val Met
            250                 255                 260 cct gct tta atc ttg acg tat ttg ggg cag ggc gcc ttg gtg atc aac      870
Pro Ala Leu Ile Leu Thr Tyr Leu Gly Gln Gly Ala Leu Val Ile Asn
                265                 270                 275 cag cct gaa gcg gtg cgc aac ccc atg ttt tat ctc gcg ccg gaa ggt      918
Gln Pro Glu Ala Val Arg Asn Pro Met Phe Tyr Leu Ala Pro Glu Gly
            280                 285                 290 ctg cgg att ccg ttg gtt att ttg gcg acc atc gct acg gtg atc gca      966
Leu Arg Ile Pro Leu Val Ile Leu Ala Thr Ile Ala Thr Val Ile Ala
    295                 300                 305 tcg cag gcc gtg att tct ggt gcg tat tca ttg acc aag cag gcc gtg     1014
Ser Gln Ala Val Ile Ser Gly Ala Tyr Ser Leu Thr Lys Gln Ala Val
310                 315                 320                 325 aat ttg aaa ctg ctg cca cgc atg gtg atc cgg cat acc tcc cgc aaa     1062
Asn Leu Lys Leu Leu Pro Arg Met Val Ile Arg His Thr Ser Arg Lys
                330                 335                 340 gag gaa ggc cag atc tat atg cca ctg gtt aat gga ttg ctg ttt gta     1110
Glu Glu Gly Gln Ile Tyr Met Pro Leu Val Asn Gly Leu Leu Phe Val
            345                 350                 355 tcc gtg atg gtt gtg gtg ctg gta ttc cga tcc tct gaa agc ctc gcc     1158
Ser Val Met Val Val Val Leu Val Phe Arg Ser Ser Glu Ser Leu Ala
        360                 365                 370 agc gcg tac gga ctt gca gtg acc gga acc ttg gtg ctg gtc agc gtc     1206
Ser Ala Tyr Gly Leu Ala Val Thr Gly Thr Leu Val Leu Val Ser Val
    375                 380                 385 ctg tat ctg atc tat gtt cac acc aca tgg tgg aaa aca gcg ctg ttc     1254
Leu Tyr Leu Ile Tyr Val His Thr Thr Trp Trp Lys Thr Ala Leu Phe
390                 395                 400                 405 att gtg ctc atc ggt att cca gaa gta ctt cta ttc gcc tcg aac acc     1302
Ile Val Leu Ile Gly Ile Pro Glu Val Leu Leu Phe Ala Ser Asn Thr
                410                 415                 420 acg aaa att cac gac ggt ggc tgg ctt cca cta ctt att gcg gcc gtg     1350
Thr Lys Ile His Asp Gly Gly Trp Leu Pro Leu Leu Ile Ala Ala Val
            425                 430                 435 ctc atc gtg gtg atg cgg acc tgg gag tgg gga agt gac cgc gtc aat     1398
Leu Ile Val Val Met Arg Thr Trp Glu Trp Gly Ser Asp Arg Val Asn
        440                 445                 450 cag gaa cgc gca gag ctg gaa ctt ccc atg gat aag ttc ttg gag aaa     1446
Gln Glu Arg Ala Glu Leu Glu Leu Pro Met Asp Lys Phe Leu Glu Lys
    455                 460                 465 ctc gat cag cca cac aat att ggt ctg cgt aaa gtt gcc gaa gtg gca     1494
Leu Asp Gln Pro His Asn Ile Gly Leu Arg Lys Val Ala Glu Val Ala
470                 475                 480                 485 gta ttt cca cat ggc acc agc gat act gtc ccg ttg tca ttg gtt cgc     1542
Val Phe Pro His Gly Thr Ser Asp Thr Val Pro Leu Ser Leu Val Arg
                490                 495                 500 tgc gtg aaa gac ctc aag ctt tta tac cga gag atc gtg atc gtt cga     1590
Cys Val Lys Asp Leu Lys Leu Leu Tyr Arg Glu Ile Val Ile Val Arg
            505                 510                 515 atc gtc caa gaa cac gtt ccg cac gtg cca cca gag gaa cgc gcg gaa     1638
Ile Val Gln Glu His Val Pro His Val Pro Pro Glu Glu Arg Ala Glu
        520                 525                 530 atg gaa gtg ctc cat cac gcc ccg atc aga gtc gtg cga gtt gat ctg     1686
Met Glu Val Leu His His Ala Pro Ile Arg Val Val Arg Val Asp Leu
    535                 540                 545
```

-continued

```
cac ctt ggt tat ttt gat gag cag aac ctg cct gag cat ctc cat gcc      1734
His Leu Gly Tyr Phe Asp Glu Gln Asn Leu Pro Glu His Leu His Ala
550                 555                 560                 565 att gac cca aca tgg gat aac gcc acc tac ttc ctg tct gcc ctg act      1782
Ile Asp Pro Thr Trp Asp Asn Ala Thr Tyr Phe Leu Ser Ala Leu Thr
                570                 575                 580 ctt cgg agc agg ttg cct gga aag att gct ggc tgg cgt gat cgt ttg      1830
Leu Arg Ser Arg Leu Pro Gly Lys Ile Ala Gly Trp Arg Asp Arg Leu
            585                 590                 595 tat ctt tcg atg gaa cgt aat cag gca tct cga act gag tct ttc aaa      1878
Tyr Leu Ser Met Glu Arg Asn Gln Ala Ser Arg Thr Glu Ser Phe Lys
        600                 605                 610 ttg caa cca agc aaa acc atc acg gtt gga aca gag ctg cac ctt          1923
Leu Gln Pro Ser Lys Thr Ile Thr Val Gly Thr Glu Leu His Leu
    615                 620                 625 taatcaggca gttgctggcc aactgagtta gcctaaaacg                           1963

<210> SEQ ID NO 2
<211> LENGTH: 628
<212> TYPE: PRT
<213> ORGANISM: Corynebacterium glutamicum ATCC13032

<400> SEQUENCE: 2

Met Leu Asn Arg Met Lys Ser Ala Arg Pro Lys Ser Val Ala Pro Lys
1               5                   10                  15

Ser Gly Gln Ala Leu Leu Thr Leu Gly Ala Leu Gly Val Val Phe Gly
            20                  25                  30

Asp Ile Gly Thr Ser Pro Leu Tyr Ser Leu His Thr Ala Phe Ser Met
        35                  40                  45

Gln His Asn Lys Val Glu Val Thr Gln Glu Asn Val Tyr Gly Ile Ile
    50                  55                  60

Ser Met Val Leu Trp Thr Ile Thr Leu Ile Val Thr Val Lys Tyr Val
65                  70                  75                  80

Met Leu Val Thr Arg Ala Asp Asn Gln Gly Gln Gly Ile Leu Ala
                85                  90                  95

Leu Val Ala Leu Leu Lys Asn Arg Gly His Trp Gly Lys Phe Val Ala
            100                 105                 110

Val Ala Gly Met Leu Gly Ala Ala Leu Phe Tyr Gly Asp Val Val Ile
        115                 120                 125

Thr Pro Ala Ile Ser Val Leu Ser Ala Thr Glu Gly Leu Thr Val Ile
    130                 135                 140

Ser Pro Ser Phe Glu Arg Phe Ile Leu Pro Val Ser Leu Ala Val Leu
145                 150                 155                 160

Ile Ala Ile Phe Ala Ile Gln Pro Leu Gly Thr Glu Lys Val Gly Lys
                165                 170                 175

Ala Phe Gly Pro Ile Met Leu Leu Trp Phe Val Thr Leu Ala Gly Leu
            180                 185                 190

Gly Ile Pro Gln Ile Ile Gly His Pro Glu Ile Leu Gln Ser Leu Ser
        195                 200                 205

Pro His Trp Ala Leu Arg Leu Ile Val Ala Glu Pro Phe Gln Ala Phe
    210                 215                 220

Val Leu Leu Gly Ala Val Val Leu Thr Val Thr Gly Ala Glu Ala Leu
225                 230                 235                 240

Tyr Ala Asp Met Gly His Phe Gly Ala Arg Pro Ile Arg Val Ala Trp
                245                 250                 255
```

Phe Cys Val Val Met Pro Ala Leu Ile Leu Thr Tyr Leu Gly Gln Gly
            260                 265                 270

Ala Leu Val Ile Asn Gln Pro Glu Ala Val Arg Asn Pro Met Phe Tyr
        275                 280                 285

Leu Ala Pro Glu Gly Leu Arg Ile Pro Leu Val Ile Leu Ala Thr Ile
    290                 295                 300

Ala Thr Val Ile Ala Ser Gln Ala Val Ile Ser Gly Ala Tyr Ser Leu
305                 310                 315                 320

Thr Lys Gln Ala Val Asn Leu Lys Leu Leu Pro Arg Met Val Ile Arg
                325                 330                 335

His Thr Ser Arg Lys Glu Glu Gly Gln Ile Tyr Met Pro Leu Val Asn
            340                 345                 350

Gly Leu Leu Phe Val Ser Val Met Val Val Leu Val Phe Arg Ser
        355                 360                 365

Ser Glu Ser Leu Ala Ser Ala Tyr Gly Leu Ala Val Thr Gly Thr Leu
    370                 375                 380

Val Leu Val Ser Val Leu Tyr Leu Ile Tyr Val His Thr Thr Trp Trp
385                 390                 395                 400

Lys Thr Ala Leu Phe Ile Val Leu Ile Gly Ile Pro Glu Val Leu Leu
                405                 410                 415

Phe Ala Ser Asn Thr Thr Lys Ile His Asp Gly Gly Trp Leu Pro Leu
            420                 425                 430

Leu Ile Ala Ala Val Leu Ile Val Val Met Arg Thr Trp Glu Trp Gly
        435                 440                 445

Ser Asp Arg Val Asn Gln Glu Arg Ala Glu Leu Glu Leu Pro Met Asp
450                 455                 460

Lys Phe Leu Glu Lys Leu Asp Gln Pro His Asn Ile Gly Leu Arg Lys
465                 470                 475                 480

Val Ala Glu Val Ala Val Phe Pro His Gly Thr Ser Asp Thr Val Pro
                485                 490                 495

Leu Ser Leu Val Arg Cys Val Lys Asp Leu Lys Leu Leu Tyr Arg Glu
            500                 505                 510

Ile Val Ile Val Arg Ile Val Gln Glu His Val Pro His Val Pro Pro
        515                 520                 525

Glu Glu Arg Ala Glu Met Glu Val Leu His His Ala Pro Ile Arg Val
530                 535                 540

Val Arg Val Asp Leu His Leu Gly Tyr Phe Asp Glu Gln Asn Leu Pro
545                 550                 555                 560

Glu His Leu His Ala Ile Asp Pro Thr Trp Asp Asn Ala Thr Tyr Phe
                565                 570                 575

Leu Ser Ala Leu Thr Leu Arg Ser Arg Leu Pro Gly Lys Ile Ala Gly
            580                 585                 590

Trp Arg Asp Arg Leu Tyr Leu Ser Met Glu Arg Asn Gln Ala Ser Arg
        595                 600                 605

Thr Glu Ser Phe Lys Leu Gln Pro Ser Lys Thr Ile Thr Val Gly Thr
    610                 615                 620

Glu Leu His Leu
625

<210> SEQ ID NO 3
<211> LENGTH: 1963
<212> TYPE: DNA
<213> ORGANISM: Corynebacterium glutamicum
<220> FEATURE:
<221> NAME/KEY: misc_feature

```
<222> LOCATION: (34)..(37)
<223> OTHER INFORMATION: putative ribosome binding site
<220> FEATURE:
<221> NAME/KEY: CDS
<222> LOCATION: (40)..(1923)
<220> FEATURE:
<221> NAME/KEY: misc_feature
<222> LOCATION: (1070)..(1070)
<223> OTHER INFORMATION: nucleobase thymine
<220> FEATURE:
<221> NAME/KEY: misc_feature
<222> LOCATION: (1924)..(1926)
<223> OTHER INFORMATION: taa stop codon

<400> SEQUENCE: 3
gtcttttctg agcgctagca tttctccact caaaggagc atg ctt aac cgc atg            54
                                            Met Leu Asn Arg Met
                                            1               5 aaa agt gcg cgg cca aaa tca gtc gct cca aaa tcc gga caa gct tta          102
Lys Ser Ala Arg Pro Lys Ser Val Ala Pro Lys Ser Gly Gln Ala Leu
        10                  15                  20 ctc act ctc ggt gcc cta ggt gtt gtg ttc ggc gac atc ggc acc agc          150
Leu Thr Leu Gly Ala Leu Gly Val Val Phe Gly Asp Ile Gly Thr Ser
            25                  30                  35 ccc ctg tac tca ctt cac act gca ttc agc atg cag cac aac aaa gtc          198
Pro Leu Tyr Ser Leu His Thr Ala Phe Ser Met Gln His Asn Lys Val
        40                  45                  50 gaa gtc act cag gaa aat gtg tac ggc atc atc tcc atg gtg ttg tgg          246
Glu Val Thr Gln Glu Asn Val Tyr Gly Ile Ile Ser Met Val Leu Trp
    55                  60                  65 acc atc act ttg atc gtc acc gtc aaa tac gtc atg ctg gtc acc cga          294
Thr Ile Thr Leu Ile Val Thr Val Lys Tyr Val Met Leu Val Thr Arg
70                  75                  80                  85 gct gac aac caa gga caa ggt ggc atc ctg gcg ctc gtt gct ttg ctg          342
Ala Asp Asn Gln Gly Gln Gly Gly Ile Leu Ala Leu Val Ala Leu Leu
                90                  95                 100 aaa aac cgt ggg cac tgg gga aaa ttc gtg gca gta gcc ggc atg ttg          390
Lys Asn Arg Gly His Trp Gly Lys Phe Val Ala Val Ala Gly Met Leu
            105                 110                 115 ggc gcc gca ttg ttt tat ggc gat gtg gtg atc acc ccg gcg atc tct          438
Gly Ala Ala Leu Phe Tyr Gly Asp Val Val Ile Thr Pro Ala Ile Ser
        120                 125                 130 gtt ctc agc gca aca gaa ggc ttg acg gtt atc tcc cca agc ttt gag          486
Val Leu Ser Ala Thr Glu Gly Leu Thr Val Ile Ser Pro Ser Phe Glu
    135                 140                 145 cgc ttc att ctg ccc gta tct ctc gca gtt ctg atc gct att ttt gca          534
Arg Phe Ile Leu Pro Val Ser Leu Ala Val Leu Ile Ala Ile Phe Ala
150                 155                 160                 165 atc caa ccg ctc ggt aca gaa aaa gtc ggc aaa gcc ttc ggc ccc atc          582
Ile Gln Pro Leu Gly Thr Glu Lys Val Gly Lys Ala Phe Gly Pro Ile
                170                 175                 180 atg ttg ctg tgg ttt gtc acc ctt gca gga ttg gga att ccg caa atc          630
Met Leu Leu Trp Phe Val Thr Leu Ala Gly Leu Gly Ile Pro Gln Ile
            185                 190                 195 atc ggg cac cca gaa atc ttg cag agc ttg tct cca cat tgg gcc ctg          678
Ile Gly His Pro Glu Ile Leu Gln Ser Leu Ser Pro His Trp Ala Leu
        200                 205                 210 cgc ttg att gtg gct gag cct ttc caa gca ttt gtg ctg ctt ggt gcc          726
Arg Leu Ile Val Ala Glu Pro Phe Gln Ala Phe Val Leu Leu Gly Ala
    215                 220                 225 gtt gtc ctg aca gta acg ggt gcg gaa gcg ctc tac gct gat atg ggc          774
Val Val Leu Thr Val Thr Gly Ala Glu Ala Leu Tyr Ala Asp Met Gly
230                 235                 240                 245
```

```
cat ttt ggg gcg agg cca atc aga gtg gcg tgg ttt tgc gtc gtc atg    822
His Phe Gly Ala Arg Pro Ile Arg Val Ala Trp Phe Cys Val Val Met
                250             255                 260 cct gct tta atc ttg acg tat ttg ggg cag ggc gcc ttg gtg atc aac    870
Pro Ala Leu Ile Leu Thr Tyr Leu Gly Gln Gly Ala Leu Val Ile Asn
                265             270                 275 cag cct gaa gcg gtg cgc aac ccc atg ttt tat ctc gcg ccg gaa ggt    918
Gln Pro Glu Ala Val Arg Asn Pro Met Phe Tyr Leu Ala Pro Glu Gly
        280             285                 290 ctg cgg att ccg ttg gtt att ttg gcg acc atc gct acg gtg atc gca    966
Leu Arg Ile Pro Leu Val Ile Leu Ala Thr Ile Ala Thr Val Ile Ala
        295             300             305 tcg cag gcc gtg att tct ggt gcg tat tca ttg acc aag cag gcc gtg    1014
Ser Gln Ala Val Ile Ser Gly Ala Tyr Ser Leu Thr Lys Gln Ala Val
310             315             320                 325 aat ttg aaa ctg ctg cca cgc atg gtg atc cgg cat acc tcc cgc aaa    1062
Asn Leu Lys Leu Leu Pro Arg Met Val Ile Arg His Thr Ser Arg Lys
                330             335                 340 gag gaa gtc cag atc tat atg cca ctg gtt aat gga ttg ctg ttt gta    1110
Glu Glu Val Gln Ile Tyr Met Pro Leu Val Asn Gly Leu Leu Phe Val
        345             350                 355 tcc gtg atg gtt gtg gtg ctg gta ttc cga tcc tct gaa agc ctc gcc    1158
Ser Val Met Val Val Val Leu Val Phe Arg Ser Ser Glu Ser Leu Ala
        360             365             370 agc gcg tac gga ctt gca gtg acc gga acc ttg gtg ctg gtc agc gtc    1206
Ser Ala Tyr Gly Leu Ala Val Thr Gly Thr Leu Val Leu Val Ser Val
        375             380             385 ctg tat ctg atc tat gtt cac acc aca tgg tgg aaa aca gcg ctg ttc    1254
Leu Tyr Leu Ile Tyr Val His Thr Thr Trp Trp Lys Thr Ala Leu Phe
390             395             400                 405 att gtg ctc atc ggt att cca gaa gta ctt cta ttc gcc tcg aac acc    1302
Ile Val Leu Ile Gly Ile Pro Glu Val Leu Leu Phe Ala Ser Asn Thr
                410             415                 420 acg aaa att cac gac ggt ggc tgg ctt cca cta ctt att gcg gcc gtg    1350
Thr Lys Ile His Asp Gly Gly Trp Leu Pro Leu Leu Ile Ala Ala Val
                425             430             435 ctc atc gtg gtg atg cgg acc tgg gag tgg gga agt gac cgc gtc aat    1398
Leu Ile Val Val Met Arg Thr Trp Glu Trp Gly Ser Asp Arg Val Asn
        440             445                 450 cag gaa cgc gca gag ctg gaa ctt ccc atg gat aag ttc ttg gag aaa    1446
Gln Glu Arg Ala Glu Leu Glu Leu Pro Met Asp Lys Phe Leu Glu Lys
        455             460                 465 ctc gat cag cca cac aat att ggt ctg cgt aaa gtt gcc gaa gtg gca    1494
Leu Asp Gln Pro His Asn Ile Gly Leu Arg Lys Val Ala Glu Val Ala
470             475             480                 485 gta ttt cca cat ggc acc agc gat act gtc ccg ttg tca ttg gtt cgc    1542
Val Phe Pro His Gly Thr Ser Asp Thr Val Pro Leu Ser Leu Val Arg
                490             495                 500 tgc gtg aaa gac ctc aag ctt tta tac cga gag atc gtg atc gtt cga    1590
Cys Val Lys Asp Leu Lys Leu Leu Tyr Arg Glu Ile Val Ile Val Arg
                505             510                 515 atc gtc caa gaa cac gtt ccg cac gtg cca cca gag gaa cgc gcg gaa    1638
Ile Val Gln Glu His Val Pro His Val Pro Pro Glu Glu Arg Ala Glu
                520             525                 530 atg gaa gtg ctc cat cac gcc ccg atc aga gtc gtg cga gtt gat ctg    1686
Met Glu Val Leu His His Ala Pro Ile Arg Val Val Arg Val Asp Leu
        535             540             545 cac ctt ggt tat ttt gat gag cag aac ctg cct gag cat ctc cat gcc    1734
His Leu Gly Tyr Phe Asp Glu Gln Asn Leu Pro Glu His Leu His Ala
```

```
                550                555                560                565
att gac cca aca tgg gat aac gcc acc tac ttc ctg tct gcc ctg act                   1782
Ile Asp Pro Thr Trp Asp Asn Ala Thr Tyr Phe Leu Ser Ala Leu Thr
                570                575                580 ctt cgg agc agg ttg cct gga aag att gct ggc tgg cgt gat cgt ttg                   1830
Leu Arg Ser Arg Leu Pro Gly Lys Ile Ala Gly Trp Arg Asp Arg Leu
                585                590                595 tat ctt tcg atg gaa cgt aat cag gca tct cga act gag tct ttc aaa                   1878
Tyr Leu Ser Met Glu Arg Asn Gln Ala Ser Arg Thr Glu Ser Phe Lys
                600                605                610 ttg caa cca agc aaa acc atc acg gtt gga aca gag ctg cac ctt                       1923
Leu Gln Pro Ser Lys Thr Ile Thr Val Gly Thr Glu Leu His Leu
                615                620                625 taatcaggca gttgctggcc aactgagtta gcctaaaacg                                        1963
```

<210> SEQ ID NO 4
<211> LENGTH: 628
<212> TYPE: PRT
<213> ORGANISM: Corynebacterium glutamicum

<400> SEQUENCE: 4

```
Met Leu Asn Arg Met Lys Ser Ala Arg Pro Lys Ser Val Ala Pro Lys
1               5                   10                  15

Ser Gly Gln Ala Leu Leu Thr Leu Gly Ala Leu Gly Val Val Phe Gly
            20                  25                  30

Asp Ile Gly Thr Ser Pro Leu Tyr Ser Leu His Thr Ala Phe Ser Met
        35                  40                  45

Gln His Asn Lys Val Glu Val Thr Gln Glu Asn Val Tyr Gly Ile Ile
    50                  55                  60

Ser Met Val Leu Trp Thr Ile Thr Leu Ile Val Thr Val Lys Tyr Val
65                  70                  75                  80

Met Leu Val Thr Arg Ala Asp Asn Gln Gly Gln Gly Gly Ile Leu Ala
                85                  90                  95

Leu Val Ala Leu Leu Lys Asn Arg Gly His Trp Gly Lys Phe Val Ala
            100                 105                 110

Val Ala Gly Met Leu Gly Ala Ala Leu Phe Tyr Gly Asp Val Val Ile
        115                 120                 125

Thr Pro Ala Ile Ser Val Leu Ser Ala Thr Glu Gly Leu Thr Val Ile
    130                 135                 140

Ser Pro Ser Phe Glu Arg Phe Ile Leu Pro Val Ser Leu Ala Val Leu
145                 150                 155                 160

Ile Ala Ile Phe Ala Ile Gln Pro Leu Gly Thr Glu Lys Val Gly Lys
                165                 170                 175

Ala Phe Gly Pro Ile Met Leu Leu Trp Phe Val Thr Leu Ala Gly Leu
            180                 185                 190

Gly Ile Pro Gln Ile Ile Gly His Pro Glu Ile Leu Gln Ser Leu Ser
        195                 200                 205

Pro His Trp Ala Leu Arg Leu Ile Val Ala Glu Pro Phe Gln Ala Phe
    210                 215                 220

Val Leu Leu Gly Ala Val Val Leu Thr Val Thr Gly Ala Glu Ala Leu
225                 230                 235                 240

Tyr Ala Asp Met Gly His Phe Gly Ala Arg Pro Ile Arg Val Ala Trp
                245                 250                 255

Phe Cys Val Val Met Pro Ala Leu Ile Leu Thr Tyr Leu Gly Gln Gly
            260                 265                 270
```

```
Ala Leu Val Ile Asn Gln Pro Glu Ala Val Arg Asn Pro Met Phe Tyr
            275                 280                 285

Leu Ala Pro Glu Gly Leu Arg Ile Pro Leu Val Ile Leu Ala Thr Ile
        290                 295                 300

Ala Thr Val Ile Ala Ser Gln Ala Val Ile Ser Gly Ala Tyr Ser Leu
305                 310                 315                 320

Thr Lys Gln Ala Val Asn Leu Lys Leu Leu Pro Arg Met Val Ile Arg
                325                 330                 335

His Thr Ser Arg Lys Glu Glu Val Gln Ile Tyr Met Pro Leu Val Asn
            340                 345                 350

Gly Leu Leu Phe Val Ser Val Met Val Val Leu Val Phe Arg Ser
        355                 360                 365

Ser Glu Ser Leu Ala Ser Ala Tyr Gly Leu Ala Val Thr Gly Thr Leu
370                 375                 380

Val Leu Val Ser Val Leu Tyr Leu Ile Tyr Val His Thr Thr Trp Trp
385                 390                 395                 400

Lys Thr Ala Leu Phe Ile Val Leu Ile Gly Ile Pro Glu Val Leu Leu
                405                 410                 415

Phe Ala Ser Asn Thr Thr Lys Ile His Asp Gly Gly Trp Leu Pro Leu
            420                 425                 430

Leu Ile Ala Ala Val Leu Ile Val Met Arg Thr Trp Glu Trp Gly
        435                 440                 445

Ser Asp Arg Val Asn Gln Glu Arg Ala Glu Leu Glu Leu Pro Met Asp
450                 455                 460

Lys Phe Leu Glu Lys Leu Asp Gln Pro His Asn Ile Gly Leu Arg Lys
465                 470                 475                 480

Val Ala Glu Val Ala Val Phe Pro His Gly Thr Ser Asp Thr Val Pro
                485                 490                 495

Leu Ser Leu Val Arg Cys Val Lys Asp Leu Lys Leu Leu Tyr Arg Glu
            500                 505                 510

Ile Val Ile Val Arg Ile Val Gln Glu His Val Pro His Val Pro Pro
        515                 520                 525

Glu Glu Arg Ala Glu Met Glu Val Leu His His Ala Pro Ile Arg Val
530                 535                 540

Val Arg Val Asp Leu His Leu Gly Tyr Phe Asp Glu Gln Asn Leu Pro
545                 550                 555                 560

Glu His Leu His Ala Ile Asp Pro Thr Trp Asp Asn Ala Thr Tyr Phe
                565                 570                 575

Leu Ser Ala Leu Thr Leu Arg Ser Arg Leu Pro Gly Lys Ile Ala Gly
            580                 585                 590

Trp Arg Asp Arg Leu Tyr Leu Ser Met Glu Arg Asn Gln Ala Ser Arg
        595                 600                 605

Thr Glu Ser Phe Lys Leu Gln Pro Ser Lys Thr Ile Thr Val Gly Thr
610                 615                 620

Glu Leu His Leu
625

<210> SEQ ID NO 5
<211> LENGTH: 1266
<212> TYPE: DNA
<213> ORGANISM: Corynebacterium glutamicum ATCC13032
<220> FEATURE:
<221> NAME/KEY: CDS
<222> LOCATION: (1)..(1263)
<220> FEATURE:
<221> NAME/KEY: misc_feature
```

<222> LOCATION: (1264)..(1266)
<223> OTHER INFORMATION: taa stop codon

<400> SEQUENCE: 5

| | | | | | | | | | | | | | | | | |
|---|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Met | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |
| gaa | cgc | att | aga | aac | gtc | gct | gaa | cgg | atc | gtt | gcc | acc | aag | aag | gct | 96 |
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |
| gga | aat | gat | gtc | gtg | gtt | gtc | tgc | tcc | gca | atg | gga | gac | acc | acg | gat | 144 |
| Gly | Asn | Asp | Val | Val | Val | Val | Cys | Ser | Ala | Met | Gly | Asp | Thr | Thr | Asp | |
| | | 35 | | | | | 40 | | | | | 45 | | | | |
| gaa | ctt | cta | gaa | ctt | gca | gcg | gca | gtg | aat | ccc | gtt | ccg | cca | gct | cgt | 192 |
| Glu | Leu | Leu | Glu | Leu | Ala | Ala | Ala | Val | Asn | Pro | Val | Pro | Pro | Ala | Arg | |
| | 50 | | | | | 55 | | | | | 60 | | | | | |
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | | 70 | | | | | 75 | | | | | 80 | |
| gtc | gcc | atg | gct | att | gag | tcc | ctt | ggc | gca | gaa | gcc | caa | tct | ttc | acg | 288 |
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | | | 115 | | | | | 120 | | | | | 125 | | | |
| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| | | 130 | | | | | 135 | | | | | 140 | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | | 150 | | | | | 155 | | | | | 160 | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | | 165 | | | | | 170 | | | | | 175 | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly | |
| | | | 195 | | | | | 200 | | | | | 205 | | | |
| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn | |
| | | 210 | | | | | 215 | | | | | 220 | | | | |
| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu | |
| 225 | | | | | 230 | | | | | 235 | | | | | 240 | |
| att | gcc | ggc | tct | atg | gag | gat | att | cct | gtg | gaa | gaa | gca | gtc | ctt | acc | 768 |
| Ile | Ala | Gly | Ser | Met | Glu | Asp | Ile | Pro | Val | Glu | Glu | Ala | Val | Leu | Thr | |
| | | | | 245 | | | | | 250 | | | | | 255 | | |
| ggt | gtc | gca | acc | gac | aag | tcc | gaa | gcc | aaa | gta | acc | gtt | ctg | ggt | att | 816 |
| Gly | Val | Ala | Thr | Asp | Lys | Ser | Glu | Ala | Lys | Val | Thr | Val | Leu | Gly | Ile | |
| | | | 260 | | | | | 265 | | | | | 270 | | | |
| tcc | gat | aag | cca | ggc | gag | gct | gcg | aag | gtt | ttc | cgt | gcg | ttg | gct | gat | 864 |
| Ser | Asp | Lys | Pro | Gly | Glu | Ala | Ala | Lys | Val | Phe | Arg | Ala | Leu | Ala | Asp | |
| | | 275 | | | | | 280 | | | | | 285 | | | | |
| gca | gaa | atc | aac | att | gac | atg | gtt | ctg | cag | aac | gtc | tct | tct | gta | gaa | 912 |
| Ala | Glu | Ile | Asn | Ile | Asp | Met | Val | Leu | Gln | Asn | Val | Ser | Ser | Val | Glu | |

-continued

```
                  290                 295                 300
gac ggc acc acc gac atc acc ttc acc tgc cct cgt tcc gac ggc cgc      960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                             1266
Ala Gly Thr Gly Arg
            420
```

<210> SEQ ID NO 6
<211> LENGTH: 421
<212> TYPE: PRT
<213> ORGANISM: Corynebacterium glutamicum ATCC13032

<400> SEQUENCE: 6

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
```

-continued

```
                    195                 200                 205
Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                    245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                    325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                    405                 410                 415

Ala Gly Thr Gly Arg
            420
```

```
<210> SEQ ID NO 7
<211> LENGTH: 1731
<212> TYPE: DNA
<213> ORGANISM: artificial sequence
<220> FEATURE:
<223> OTHER INFORMATION: Corynebacterium glutamicum DNA equipped with
      recognition sites for the restriction endonuclease XbaI
      (polynucleotide kup_G344V)
<220> FEATURE:
<221> NAME/KEY: misc_feature
<222> LOCATION: (4)..(9)
<223> OTHER INFORMATION: recognition site for restriction endonuclease
      XbaI
<220> FEATURE:
<221> NAME/KEY: misc_feature
<222> LOCATION: (866)..(866)
<223> OTHER INFORMATION: nucleobase thymine
<220> FEATURE:
<221> NAME/KEY: misc_feature
<222> LOCATION: (1723)..(1728)
<223> OTHER INFORMATION: recognition site for restriction endonuclease
      XbaI

<400> SEQUENCE: 7
gcgtctagaa atgtgtacgg catcatctcc atggtgttgt ggaccatcac tttgatcgtc    60
accgtcaaat acgtcatgct ggtcacccga gctgacaacc aaggacaagg tggcatcctg   120
gcgctcgttg ctttgctgaa aaaccgtggg cactggggaa aattcgtggc agtagccggc   180
atgttgggcg ccgcattgtt ttatggcgat gtggtgatca ccccggcgat ctctgttctc   240
agcgcaacag aaggcttgac ggttatctcc ccaagctttg agcgcttcat tctgcccgta   300
```

-continued

```
tctctcgcag ttctgatcgc tatttttgca atccaaccgc tcggtacaga aaaagtcggc      360
aaagccttcg gccccatcat gttgctgtgg tttgtcaccc ttgcaggatt gggaattccg      420
caaatcatcg ggcacccaga aatcttgcag agcttgtctc acattgggc cctgcgcttg       480 attgtggctg agccttttcca agcatttgtg ctgcttggtg ccgttgtcct gacagtaacg     540
ggtgcggaag cgctctacgc tgatatgggc cattttgggg cgaggccaat cagagtggcg      600
tggttttgcg tcgtcatgcc tgctttaatc ttgacgtatt tggggcaggg cgccttggtg      660
atcaaccagc ctgaagcggt gcgcaacccc atgttttatc tcgcgccgga aggtctgcgg      720
attccgttgg ttattttggc gaccatcgct acggtgatcg catcgcaggc cgtgatttct      780
ggtgcgtatt cattgaccaa gcaggccgtg aatttgaaac tgctgccacg catggtgatc      840
cggcatacct cccgcaaaga ggaagtccag atctatatgc cactggttaa tggattgctg      900
tttgtatccg tgatggttgt ggtgctggta ttccgatcct ctgaaagcct cgccagcgcg      960
tacggacttg cagtgaccgg aaccttggtg ctggtcagcg tcctgtatct gatctatgtt     1020
cacaccacat ggtggaaaac agcgctgttc attgtgctca tcggtattcc agaagtactt     1080
ctattcgcct cgaacaccac gaaaattcac gacggtggct ggcttccact acttattgcg     1140
gccgtgctca tcgtggtgat gcggacctgg gagtggggaa gtgaccgcgt caatcaggaa     1200
cgcgcagagc tggaacttcc catggataag ttcttggaga aactcgatca gcccacacaat    1260 attggtctgc gtaaagttgc cgaagtggca gtatttccac atggcaccag cgatactgtc     1320
ccgttgtcat tggttcgctg cgtgaaagac ctcaagcttt tataccgaga atcgtgatc      1380 gttcgaatcg tccaagaaca cgttccgcac gtgccaccag aggaacgcgc ggaaatggaa     1440
gtgctccatc acgccccgat cagagtcgtg cgagttgatc tgcaccttgg ttatttgat     1500 gagcagaacc tgcctgagca tctccatgcc attgacccaa catgggataa cgccacctac     1560
ttcctgtctg ccctgactct tcggagcagg ttgcctggaa agattgctgg ctggcgtgat     1620
cgtttgtatc tttcgatgga acgtaatcag gcatctcgaa ctgagtcttt caaattgcaa     1680
ccaagcaaaa ccatcacggt tggaacagag ctgcaccttt aatctagagc c             1731
```

<210> SEQ ID NO 8
<211> LENGTH: 20
<212> TYPE: DNA
<213> ORGANISM: artificial sequence
<220> FEATURE:
<223> OTHER INFORMATION: primer LC-NCgl0682_1

<400> SEQUENCE: 8
atcagataca ggacgctgac      20

<210> SEQ ID NO 9
<211> LENGTH: 20
<212> TYPE: DNA
<213> ORGANISM: artificial sequence
<220> FEATURE:
<223> OTHER INFORMATION: primer LC-NCgl0682_2

<400> SEQUENCE: 9
aggtctgcgg attccgttgg      20

<210> SEQ ID NO 10
<211> LENGTH: 20
<212> TYPE: DNA
<213> ORGANISM: artificial sequence
<220> FEATURE:

```
<223> OTHER INFORMATION: probe NCgl0682_344_C

<400> SEQUENCE: 10
tagatctgga cttcctcttt                                           20

<210> SEQ ID NO 11
<211> LENGTH: 35
<212> TYPE: DNA
<213> ORGANISM: artificial sequence
<220> FEATURE:
<223> OTHER INFORMATION: probe NCgl0682_344_A

<400> SEQUENCE: 11
cacggataca aacagcaatc cattaaccag tggca                          35
```